US005760264A

United States Patent [19]

Brieden

[11] Patent Number: 5,760,264
[45] Date of Patent: Jun. 2, 1998

[54] PROCESS FOR PREPARING OPTICALLY ACTIVE METALLOCENYL-PHOSPHINES

[75] Inventor: Walter Brieden, Glis, Switzerland

[73] Assignee: Lonza, AG, Gampel/Wallis, Switzerland

[21] Appl. No.: 836,978

[22] PCT Filed: Nov. 28, 1995

[86] PCT No.: PCT/EP95/04678

§ 371 Date: Jul. 9, 1997

§ 102(e) Date: Jul. 9, 1997

[87] PCT Pub. No.: WO96/16971

PCT Pub. Date: Jun. 6, 1996

[30] Foreign Application Priority Data

Nov. 29, 1994 [CH] Switzerland ............................ 3598/94

[51] Int. Cl.$^6$ ................. C07F 17/02; C07F 15/02; B01J 31/00
[52] U.S. Cl. ..................... 556/22; 502/162; 556/144; 556/148
[58] Field of Search .................. 556/22, 144, 148; 502/162

[56] References Cited

FOREIGN PATENT DOCUMENTS 0 305 180   3/1989   European Pat. Off. .

OTHER PUBLICATIONS

Hayashi et al., J. Organomet. Chem., vol. 370, Nos. 1 to 3 (1989) pp. 129 to 139.

Marquarding et al., J. Am. Chem. Soc., vol. 92, No. 18, (1970), pp. 5389 to 5393.

C. R. Hauser and J. K. Lindsay, J. Am. Chem., (1957), 22, 482.

Lambusta et al., Tetrahedron: Asymmetry, vol. 4, (5) pp. 919–924.

Hayashi et al., Bull. Chem. Soc. Jpn., vol. 4, No. 5, (1980), pp. 1138–1151.

*Primary Examiner*—Porfirio Nazario-Gonzalez
*Attorney, Agent, or Firm*—Fisher, Christen & Sabol

[57] ABSTRACT

Disclosed is a novel method of producing optically active metallocenyl phosphines of the general formula shown In the formula (Ia) (Ib), M represents iron, ruthenium or nickel; $R^1$ and $R^{1'}$ both represent $C_1$–$C_4$ alkyl groups; $R^2$ and $R^3$ each represent independently of each other either hydrogen or a $C_1$–$C_4$ alkyl group, or, together with the nitrogen atom, form a five- or six member saturated heterocyclic ring which may optionally contain further heteroatoms; $R^4$ and $R^5$ each represent independently of each other a $C_1$–$C_4$ alkyl group (for example) or an aryl group which is optionally substituted with one or more methyl or methoxy groups or with one or more fluorine atoms. These are obtained from acyl- or 1,1'-diacylmetallocenes by enantioselective reduction with borane in the presence of optically active oxazoborolidines, esterification of the metallocenyl alkanols thus obtained, nucleophilic substitution of the ester group with a secondary amine, lithiation and reaction with a phosphine halide.

22 Claims, No Drawings

PROCESS FOR PREPARING OPTICALLY ACTIVE METALLOCENYL-PHOSPHINES

BACKGROUND OF THE INVENTION

Field of the Invention

The present invention relates to a process for preparing optically active metallocenylphosphines from prochiral acylmetallocenes.

BACKGROUND OF THE ART

Optically active phosphines are being used to an increasing extent as ligands for chiral transition metal complexes. The latter are in turn used as catalysts in homogeneously catalyzed enantioselective reactions ("asymmetric syntheses").

Optically active phosphines used include, in particular, metallocenylphosphines having chiral substituents on the cyclopentadiene ring. An important group of such metallocenylphosphines is represented by the general formulae

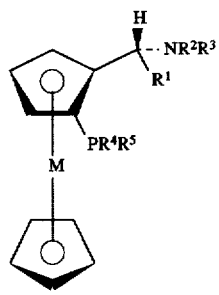

Ia

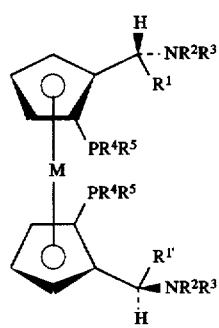

Ib and their mirror images.

In these formulae, M is iron, ruthenium or nickel; $R^1$ and $R^{1'}$ are identical or different and are each a $C_1$–$C_4$-alkyl group, a $C_1$–$C_4$-perfluoroalkyl group, a $C_2$–$C_4$-alkenyl group, a $C_3$–$C_6$-cycloalkyl group or an unsubstituted or substituted acyl group; $R^2$ and $R^3$ are either, independently of one another, hydrogen or a $C_1$–$C_4$-alkyl group or together with the nitrogen atom form a five- or six-membered saturated heterocyclic ring which may also contain further heteroatoms; $R^4$ and $R^5$ are each, independently of one another, a $C_1$–$C_4$-alkyl group, a $C_3$–$C_6$-cycloalkyl group or an aryl group which may be unsubstituted or substituted by one or more methyl or methoxy groups or by one or more fluorine atoms, or $R^4$ and $R^5$ together with the phosphorus atom form a saturated five- or six-membered heterocyclic ring. Here and in the following, $C_1$–$C_4$-alkyl groups are in each case unbranched and branched primary, secondary and tertiary alkyl groups having up to four carbon atoms, i.e. methyl, ethyl, propyl, isopropyl, butyl, isobutyl, sec-butyl and tert-butyl. $C_1$–$C_4$-Perfluoroalkyl groups are the corresponding perfluorinated groups, preferably trifluoromethyl.

$C_2$–$C_4$-Alkenyl groups are, for example, vinyl, allyl, propenyl, 1-butenyl, 2-butenyl, 3-butenyl and isopropenyl; $C_3$–$C_6$-cycloalkyl is cyclopropyl, cyclobutyl, cyclopentyl and preferably cyclohexyl. Aryl groups are monocyclic and polycyclic aromatic hydrocarbon radicals, in particular phenyl and naphthyl. Examples of such metallocenylphosphines and their use may be found, inter alia, in T. Hayashi et al., Bull. Chem. Soc. Jpn. 1980, 53, 1138–1151 (M=Fe).

The compounds of the formulae Ia and Ib each contain not only the chiral centre at the carbon atom adjacent to $R^1$ but also a chiral plane through the 1,2-disubstituted cyclopentadiene ring. However, among the possible stereoisomers, the introduction of the phosphino group forms only those in which both chirality elements have the opposite configuration, i.e. the $(R^*,S^*)$ stereoisomers according to the convention employed in Chemical Abstracts. Here and in the following, the S—$(R^*,S^*)$ stereoisomer, in which the absolute configuration in respect of the chiral plane is S, is depicted in each case.

If the two substituents $R^4$ and $R^5$ on the phosphorus atom are different, the latter forms an additional chiral centre.

The previous processes for preparing the optically active metallocenylphosphines of the formula I (see, for example, B. T. Hayashi et al., loc. cit.) generally require racemate resolution of a precursor (cf. D. Marquarding et al., J. Am. Chem. Soc. 1970, 92, 5389).

This racemate resolution requires not only a considerable outlay, but also reduces the yield because, as a rule, only one of the two enantiomers is required and the other may be regarded as waste.

BROAD DESCRIPTION OF THE DESCRIPTION

It is an object of the present invention to open up a route to the optically active metallocenylphosphines of the formula Ia/Ib which does without racemate resolution and makes it possible to prepare the S—$(R^*,S^*)$ stereoisomer depicted or its mirror image as required in a targeted manner.

According to the invention, this object is achieved by the processes of the invention.

It has been found that acylmetallocenes of the general formulae

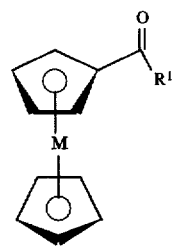

IIa

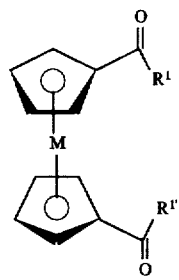

IIb where M is iron, ruthenium or nickel and $R^1$ and $R^{1'}$ are each, independently of one another, a $C_1$–$C_4$-alkyl group, a $C_1$–$C_4$-perfluoroalkyl group, a $C_2$–$C_4$-alkenyl group, a $C_3$–$C_6$-cycloalkyl group or an unsubstituted or substituted aryl group, can be enantioselectively reduced in good optical yield using borane or another hydroboration agent in the presence of an optically active oxazaborolidine of the formula

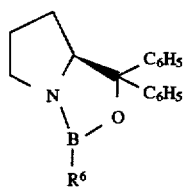

III where $R^6$ is hydrogen, $C_1$–$C_4$-alkyl or phenyl, to give the corresponding metallocenylalkanols of the general formulae

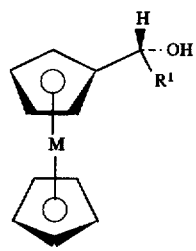

IVa

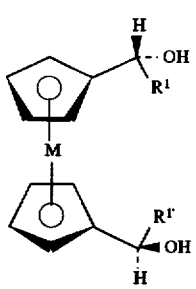

IVb where M, $R^1$ and R3 are as defined above. This requires 0.5 mol of borane per 1 mol of monoacylmetallocene, corresponding to 1 mol of borane or an equivalent amount of hydroboration agent per 1 mol of diacylmetallocene. A larger excess of borane is to be avoided because it has surprisingly been found that a further reduction takes place in the presence of excess borane to give alkyl-metallocenes.

The acylmetallocenes of the formulae IIa/IIb can be prepared by known processes or methods similar thereto, for example acetylferrocene by a method of C. R. Hauser and J. K. Lindsay, J. Org. Chem. 1957, 22, 482. An overview of the preparation of acylmetallocenes may be found, for example, in P. L. Pauson, Methoden Org. Chem. (Houben-Weyl), Volume E18, part 1, pp. 223–450. Some acylmetallocenes are also commercially available.

As acylmetallocenes, preference is given to using the acylferrocenes.

Preference is given to using acylmetallocenes of the formula IIa or IIb whose acyl groups are acetyl groups, i.e. $R^1$ (=$R^{1'}$)=methyl.

The optically active oxazaborolidines of the formula III used as catalyst are known from EP-A 0 305 180 and can be prepared starting from the natural amino acid L-proline, with the (S) configuration shown in formula III being obtained. Correspondingly, the "unnatural" D-proline gives the (R) configuration which is the mirror image of formula III and whose use in the process of the invention correspondingly also gives the metallocenylalkanols of the formula IVa or IVb and all subsequent stages in the mirror-image form.

If the oxazaborolidine (III) used is the compound in which $R^6$ is hydrogen, it is preferably prepared in situ directly from the optically active α,α-diphenyl-2-pyrrolidinomethanol and borane.

The borane is preferably used in the form of a stable adduct, for example with dimethyl sulphide, tetrahydrofuran or 1,4-oxathiane. Particular preference is given to the adduct with dimethyl sulphide. In place of borane, a mixture of $NaBH_4$ and $(CH_3)_3SiCl$ can also be advantageously used as hydroboration agent.

For the further conversion into the metallocenylphosphines of the formula I, the metallocenylalkanols of the formula IV are advantageously first esterified. The esterification of the hydroxy group introduces a leaving group into the molecule which group can be replaced by nucleophilic substitution in the subsequent step of the synthesis. Suitable leaving groups in this case are not only the otherwise customary groups such as tosyl (p-toluenesulphonyl) and related groups, but preferably also acetyl. The introduction of the acetyl groups can be achieved in a customary manner, for example using acetic anhydride in the presence of pyridine.

In the next stage, the ester function is replaced nucleophilically by reaction with an amine, with the configuration of the chiral centre being retained because of the particular circumstances in the metallocene system.

The amine used is an amine of the general formula $HNR^2R^3$ (V), where $R^2$ and $R^3$ are as defined above. Such amines include, in particular, ammonia, monoalkylamines and dialkylamines having $C_1$–$C_4$-alkyl groups, five- and six-membered, saturated nitrogen heterocycles such as pyrrolidine and piperidine or saturated nitrogen heterocycles containing further hetero atoms, for example morpholine. The amine used is preferably a secondary amine, in particular dimethylamine.

The resulting metallocenylamine of the general formula

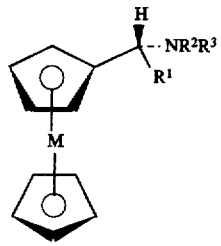

VIa or

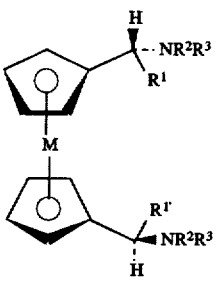

VIb is finally, in the last stage, lithiated and then reacted with a halophosphine of the general formula

X PR⁴R⁵      VII where X is chlorine, bromine or iodine and $R^4$ and $R^5$ are as defined above.

X is preferably chlorine; $R^4$ and $R^5$ are preferably identical and each a phenyl group.

The lithiation is preferably carried out using n-butyllithium in an inert solvent.

DETAILED DESCRIPTION OF THE INVENTION

The following examples clarify the procedure of the process of the invention, without implying a restriction.

EXAMPLE 1

(R)-(1-Hydroxyethyl)ferrocene (Formula IVa, M=Fe, $R^1$=methyl)

In a 10 l flask, a solution of 60.8 g (0.24 mol) of (S)-α,α-diphenylprolinol in 100 ml of tetrahydrofuran was stirred for 38 hours with 30 ml of borane-dimethyl sulphide adduct under argon at room temperature.

Subsequently, 1.0 l of tetrahydrofuran and 750 g (3.29 mol) of acetylferrocene (dried overnight at 40° C. in vacuo) were added to the catalyst solution thus obtained and dissolved by further addition of 1.0 l of tetrahydrofuran. The amount of catalyst was thus 6.8 mol%. At 20°–25° C., a further 145 ml of borane-dimethyl sulphide adduct (1.75 mol altogether) was added dropwise and uniformly over a period of 3 hours. After stirring for a further 30 minutes, the reaction mixture was hydrolysed while cooling by addition of 2.0 l of water, with care being taken to ensure that the temperature did not rise above 30° C. Subsequently, 2.0 l of tert-butyl methyl ether were added, the phases were separated and the aqueous phase was extracted once more with 1.0 l of tert-butyl methyl ether. The combined organic phases were dried over magnesium sulphate and the solvent was distilled off.

The resulting crude (R)-(1-hydroxyethyl)ferrocene was used without purification for the next stage.

EXAMPLE 2

(R)-(1-Acetoxyethyl)ferrocene 500 g (6.32 mol) of pyridine and subsequently 600 g (5.88 mol) of acetic anhydride were added dropwise while stirring to the crude (R)-(1-hydroxyethyl) ferrocene from Example 1 at 25° C. under argon. The reaction mixture was allowed to stand for a further 20 hours at 25° C., then hydrolysed with 1.5 l of ammonium chloride solution (20%) and extracted three times with 1.5 l each time of ethyl acetate. The solvent was distilled off from the combined organic phases.

Yield: 812 g (91%, based on acetylferrocene) Optical purity: 88% ee (HPLC)

EXAMPLE 3

(R)-[1-(Dimethylamino)ethyl]ferrocene (Formula VIa, M=Fe, $R^1$=$R^2$=$R^3$=methyl)

In a 10 l flask, 812 g of crude (R)-1-acetoxyethylferrocene from Example 2 was admixed under argon at 25° C. while stirring with 1.0 l of 50% strength aqueous dimethylamine solution and 1.0 l of methanol, with the temperature rising to 40° C. The reaction mixture was subsequently allowed to stand for 2 days at 25° C. The mixture was then evaporated at 50° C. in a waterpump vacuum to 1.1 kg and the residue was added to 2.0 l of 20% strength sodium hydroxide solution.

The resulting mixture was extracted three times with 1.0 l each time of dichloromethane and the combined organic phases were dried using magnesium sulphate. Distilling off the solvent gave the crude (R)-[1-(dimethylamino)ethyl] ferrocene as a dark brown oil.

Yield 743 g (97%)

EXAMPLE 4

[S-(R*,S*)]-[1-(Dimethylamino)ethyl]-2-(diphenylphosphino)ferrocene (Formula Ia, M=Fe, $R^1$=$R^2$=$R^3$=methyl, $R^4$=$R^5$=phenyl)

A 10 l flask was charged under argon with 400 g (1.56 mol) of (R)-[1-(dimethylamino)ethyl]ferrocene from Example 3 in 3.5 l of tert-butyl methyl ether. At 25° C., 1.22 l (3.10 mol) of n-butyllithium (2.55M in hexane) were added dropwise over a period of 1 hour while stirring. To complete the metallation, stirring was continued for 1 hour and subsequently 619 g (2.80 mol) of chlorodiphenylphosphine were added dropwise at 20°–45° C. over a period of 30 minutes and the mixture was finally heated under reflux for a further 2.5 hours. After cooling to 15° C., the mixture was hydrolysed with 1.8 l of sodium hydrogen carbonate solution (80 g of $NaHCO_3$) at 20° C. After addition of 0.4 l of dichloromethane, the mixture was filtered through Celite®. The filtration residue was washed with a further 1.0 l of dichloromethane. The organic phase of the filtrate was separated off and washed with 0.4 l of water. The combined organic phases were extracted three times with a total of 4.0 l of dichloromethane. The combined organic phases were dried over magnesium sulphate and evaporated at atmospheric pressure to about 1 l. 1.5 l of ethanol were added to the brown residue and the mixture was stirred overnight at about 0° C. The precipitated solid product was filtered off, washed with 0.5 l of methanol at 0° C. and dried.

Yield: 325 g (47%), orange crystals (yield based on acetylferrocene: 42%) M.p.: 136.7°–139.1° C. $[\alpha]^0$=–368.8 (c=0.6, ethanol) Optical purity: >98% ee.

EXAMPLE 5–8

The procedure of Example 1 was repeated using various amounts of oxazaborolidine (III, $R^6$=H) prepared in situ from (S)-α,α-diphenylprolinol and borane or the corresponding B-methyl compound (III, $R^6$=$CH_3$) prepared as described in EP-A 0 305 180 and the optical purity of the product was determined. The following results were obtained:

Example 5: Catalyst: $R^6$=H, amount used: 2.3 mol %, optical purity: 54% ee.

Example 6: Catalyst: $R^6$=H, amount used: 4.5 mol %, optical purity: 76% ee.

Example 7: Catalyst: $R^6$=$CH_3$, amount used: 4.5 mol %, optical purity: 78% ee.

Example 8: Catalyst: $R^6$=$CH_3$, amount used: 7.3 mol %, optical purity: 78% ee.

EXAMPLE 9

(R)-(1-Hydroxypropyl)ferrocene (Formula IVa, M=Fe, $R^1$=ethyl)

2.5 ml (25 mmol) of borane-dimethyl sulphide adduct were added dropwise at 20°C to a solution of 10.0 g (41.3 mmol) of propionylferrocene and 2.5 ml (2.5 mmol, 0.06 eq) of catalyst (S)-III ($R^6$=$CH_3$) in 30 ml of tetrahydrofuran over a period of 30 minutes. After 1 hour at 20°–25° C., the reaction mixture was poured while stirring vigorously onto about 200 ml of ice/water and stirred for 0.5 hours. The aqueous phase was subsequently extracted three times with 200 ml each time of tert-butyl methyl ether, the combined organic phases were dried over magnesium sulphate and evaporated in a high vacuum. This gave 10.7 g (106%) of the crude title compound. This crude product can be used without further purification for the further reactions.

Optical purity: 96% ee (HPLC).

$^1$H NMR (400 MHz, $CDCl_3$): δ=4.27–4.21 (m, 2H), 4.21–4.12 (m, 3H), 4.17 (s, 5H), 1.96 (br. s, 1H), 1.75–1.60 (m, 2H), 0.94 (t, J=7.4 Hz, 3H).

$^{13}$C NMR (100 MHz, $CDCl_3$): δ=94.32, 71.10, 68.26, 67.84, 67.69, 67.27, 65.22, 31.06, 10.37.

EXAMPLE 10

(R)-[1-(Dimethylamino)propyl]ferrocene (Formula VIa, M=Fe, R$^1$=ethyl, R$^2$=R$^3$=methyl)

A solution of 10.0 g (38.6 mmol) of crude (R)-(1-hydroxypropyl)ferrocene in 10 ml of pyridine and 10 ml of acetic anhydride was stirred at room temperature for 18 hours. The reaction mixture was admixed with 50 ml of water and extracted three times with 200 ml each time of diethyl ether. The combined organic phases were dried over magnesium sulphate and evaporated on a rotary evaporator. The formation of the acetylated (R)-(1-hydroxypropyl) ferrocene can be followed by $^1$H NMR spectroscopy ($\delta_{CHOAc}$=5.72–5.66, "dd", 1H). The crude (R)-(1-acetoxypropyl) ferrocene was stirred overnight at room temperature with 100 ml of isopropyl alcohol and 75 ml of dimethylamine (50% in water). The mixture was subsequently subjected to an aqueous work-up and extracted three times with 200 ml each time of diethyl ether. The combined organic phases were dried over magnesium sulphate and evaporated to dryness.

Yield: 9.10 g (87%) of brown oil (crude product) which slowly crystallized.

$^1$H NMR (400 MHz, CDCl$_3$): $\delta$=4.20–4.08 (m, 2H), 4.10 (s, 5H), 4.08–4.06 (m, 1H), 4.02–4.01 (m, 1H), 3.27–3.23 ("dd", 1H), 2.10–1.96 (m, 1H), 2.00 (s, 6H), 1.79–1.67 (m, 1H), 1.10 (t, J=7.5 Hz, 3H)

EXAMPLE 11

[S-(R*,S*)]-1-[1-(Dimethylamino)propyl]-2-(diphenylphosphino) ferrocene (Formula Ia, M=Fe, R$^1$=ethyl, R$^2$=R$^3$=methyl, R$^4$=R=phenyl)

32.5 ml (188 mmol) of n-butyllithium (2.7M in hexane) were added dropwise at room temperature to a solution of 9.53 g (35 mmol) of (R)-[1-(dimethylamino)propyl] ferrocene in 60 ml of tert-butyl methyl ether over a period of 0.5 hour and the mixture was stirred further for 1 hour. It was subsequently heated under reflux for 30 minutes until gas evolution could no longer be observed. 13.0 ml (70 mmol) of P-chlorodiphenylphosphine were added dropwise at 25°–35° C. and the mixture was subsequently heated under reflux for 4 hours. After a further 16 hours at room temperature, the reaction mixture was poured onto 200 ml of ice/water and stirred for 0.5 hour. The resulting mixture was extracted three times with 150 ml each time of diethyl ether and the combined organic phases were evaporated on a rotary evaporator to give 24.4 g of residue which was recrystallized from ethanol.

Yield: 6.03 g (38%) of orange crystals. M.p.: 139.5°–140.5° C. [a]=−384.3 (c=1, CHCl$_3$).

$^1$H NMR (400 MHz, CDCl$_3$): $\delta$=7.63–7.56 (m, 2H), 7.36–7.32 (m, 3H), 7.25–7.14 (m, 5H), 4.32–4.29 (m, 1H), 4.27–4.24 (m, 1H), 3.92–3.88 (m, 1H), 3.90 (s, 5H), 3.88–3.83 (m, 1H), 1.88–1.75 (m, 2H), 1.78 (s, 6H), 1.18 (t, J=7.4 Hz, 3H).

$^{13}$C NMR (100 MHz, CDCl$_3$): $\delta$=140.99 (J$_{PC}$=13 Hz), 139.33 (J$_{PC}$=12 Hz), 135.30 (J$_{PC}$=21 Hz), 132.36 (J$_{PC}$=19 Hz), 128.67, 127.86 (J$_{PC}$=7 Hz), 127.37 (J$_{PC}$=6 Hz), 127.16, 96.86 (J$_{PC}$=23 Hz), 76.24 (J$_{PC}$=8 Hz), 71.45 (J$_{PC}$=6 Hz), 69.72, 69.63, 68.27, 63.33 (JPC=6 Hz), 39.64, 22.05, 13.52.

EXAMPLE 12

(R,R)-1,1'-Bis(1-hydroxyethyl)ferrocene (Formula IVb, M=Fe, R$^1$=R$^{1'}$=methyl)

11.5 ml (115 mmol) of borane-dimethyl sulphide adduct were added dropwise at 20° C. to a solution of 30.0 g (111 mmol) of 1,1'-diacetylferrocene and 13.5 ml (13.5 mmol, 0.12 eq) of catalyst (S)-III (R$^6$=CH$_3$) in 200 ml of tetrahydrofuran over a period of 45 minutes. After 1 hour at 20°–25° C., the reaction mixture was poured while stirring vigorously onto about 600 ml of ice/water and stirred for 0.5 hour. The aqueous phase was subsequently extracted three times with 200 ml each time of tert-butyl methyl ether, the combined organic phases were dried over magnesium sulphate and evaporated in a high vacuum. This gave 32.7 g (107%) of the crude title compound. This crude product can be used without further purification for the further reactions. Recrystallization from hexane gave (R,R)-1,1'-bis(1-hydroxyethyl)ferrocene as a yellow crystalline solid.

Optical purity:>99% ee (HPLC).

(S,S)-1,1'-Bis(1-hydroxyethyl)ferrocene can be obtained by a similar method from 1,1'-diacetylferrocene and (R)-III (R$^6$=CH$_3$).

M.p.: 71.8°–72.5° C.

$^1$H NMR (400 MHz, CDCl$_3$): $\delta$=4.65 (q, J=6.3 Hz, 2H), 4.22–4.10 (m, 10H), 1.39 (d, J=6.3 Hz, 6H).

$^{13}$C NMR (100 MHz, CDCl$_3$): $\delta$=95.27, 67.71, 67.62, 66.17, 66.05, 65.64, 25.54.

EXAMPLE 13

(S,S)-1,1'-Bis(1-acetoxyethyl)ferrocene 4.0 ml of pyridine and 4.0 ml of acetic anhydride were added to 4.00 g (14.6 mmol) of (S,S)-1,1'-bis(1-hydroxyethyl)ferrocene and the resulting solution was stirred overnight at 25° C. After hydrolysis of the excess anhydride using 100 ml of water, the hydrolysis mixture was extracted twice with 200 ml each time of diethyl ether and the combined organic extracts were dried over magnesium sulphate. The solvent was taken off and the residue was dried to constant weight in a high vacuum.

Yield: 4.83 g (92%) of dark brown oil (crude product) which slowly crystallized.

$^1$H NMR (400 MHz, CDCl$_3$): $\delta$=5.82 (q, J=6.8 Hz, 2H), 4.24 (m, 2H), 4.18 (m, 2H), 4.13 (m, 4H), 2.05 (s, 6), 1.54 (d, J=6.8 Hz, 6H).

$^{13}$C NMR (100 MHz, CDCl$_3$): $\delta$=170.46, 88.85, 69.23, 68.94, 68.87, 68.64, 66.69, 21.37, 20.34.

EXAMPLE 14

(R,R)-1,1'-Bis[1-(dimethylamino)ethyl]ferrocene (Formula VIb, M=Fe, R$^1$=R$^{1'}$=R$^2$=R$^3$=methyl)

32.7 g (about 111 mmol) of crude (R,R)-1,1'-bis(1-hydroxyethyl)ferrocene were dissolved in 30 ml of pyridine and admixed with 30 ml of acetic anhydride. After stirring for 16 hours at 25° C., the excess anhydride was hydrolysed with 200 ml of ice water and the mixture was extracted three times with 100 ml each Time of diethyl ether. The combined organic phases were washed once more with about 150 ml of water, dried over magnesium sulphate and evaporated. The residue was admixed with 200 ml of hexane and the solvent was removed on a rotary evaporator (<40° C). This procedure was repeated two more times. The resulting dark brown oil was dissolved in 200 ml of isopropyl alcohol and admixed with 120 ml of dimethylamine (50% in water). After stirring at 25° C. (16 hours), 200 ml of water were added and the pH of the reaction mixture was adjusted to 1 using 100 ml of 32% strength HCl and the aqueous phase was washed twice with 100 ml each time of diethyl ether.

The aqueous phase was basified with sodium hydroxide solution (40% strength) to a pH of 12–14 and extracted three times with 100 ml each time of diethyl ether. The combined organic phases were dried over magnesium sulphate and evaporated. In order to remove isopropyl alcohol still present, the oil obtained was admixed with about 100 ml of hexane and again evaporated on a rotary evaporator. This procedure was repeated two more times. Drying in a high vacuum gave 24.1 g (66%, based on 1,1'-diacetylferrocene) of the title compound in the form of a dark brown oil. (Without hydrochloric acid treatment, the yield rises to 86%).

$^1$H NMR (400 MHz, CDCl$_3$): δ=4.11–4.01 (m, 8H), 3.60 (q, J=6.9 Hz, 2H), 2.08 (s, 12H), 1.44 (s, 6H).

EXAMPLE 15

2,2'-Bis[(R)-1-(dimethylamino)ethyl]-(S,S)-1,1'-bis (diphenylphosphino)ferrocene (Formula Ib, M=Fe, R$^1$=R$^{1'}$=R$^2$=R$^3$=methyl, R$^4$=R$^5$=phenyl)

20.0 g (60.9 mmol) of (R,R)-1,1'-bis[1-(dimethylamino) ethyl]ferrocene were dissolved in 200 ml of tert-butyl methyl ether and admixed with 67.7 ml (183 mmol) of n-butyllithium (2.7M in hexane) and stirred for 2.5 hours at room temperature. Subsequently, 40.6 ml (213 mmol) of P-chlorodiphenylphosphine were slowly added dropwise under reflux over a period of 0.5 hour and the mixture was heated under reflux for 2 hours. After cooling to 20° C., the reaction mixture was poured into about 600 ml of saturated sodium hydrogen carbonate solution and extracted twice with 400 ml each time of toluene. The combined organic phases were dried over magnesium sulphate and partially evaporated. The reddish brown solution was heated with 6 g of activated charcoal for 1 hour at 80° C., subsequently filtered and evaporated to dryness. The residue was taken up in 300 ml of methanol and filtered. After drying, 29.4 g (69%) of the title compound were isolated as a pale yellow powder.

$^1$H NMR (400 MHz, CDCl$_3$): δ=7.78–7.08 (m, 20H), 4.33 (m, 2H), 4.14 (m, 2H), 4.06 ("dq", 2H), 3.05 (m, 2H), 1.71 (s, 12H), 1.26 (q, J=7 Hz, 6H).

I claim:

1. Process for preparing optically active metallocenylphosphines of the general formulae

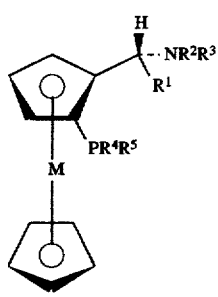
Ia

-continued
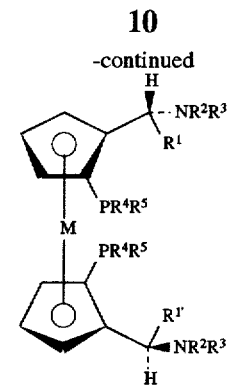
Ib and their mirror images, where M is iron, ruthenium or nickel; and R$^1$ and R$^{1'}$ are each, independently of one another, a C$_1$–C$_4$-alkyl group, a C$_1$–C$_4$-perfluoroalkyl group, a C$_2$–C$_4$-alkenyl group, a C$_3$–C$_6$-cycloalkyl group or an unsubstituted or substituted aryl group;

R$^2$ and R$^3$ are either, independently of one another, hydrogen or a C$_1$–C$_4$-alkyl group or R$^2$ and R$^3$ together with the nitrogen atom form a five- or six-membered saturated heterocyclic ring which may contain further heteroatoms; and R$^4$ and R$^5$ are each, independently of one another, a C$_1$–C$_4$-alkyl group, a C$_3$–C$_6$-cycloalkyl group or an aryl group which may be unsubstituted or substituted by one or more methyl or methoxy groups or by one or more fluorine atoms, or R$^4$ and R$^5$ together with the phosphorus atom form a saturated five- or six-membered heterocyclic ring, characterized in that, in a first stage, an acylmetallocene of the general formula

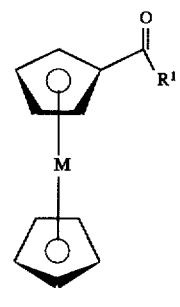
IIa or

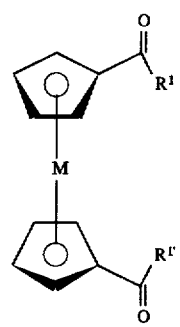
IIb where M, R$^1$ and R$^{1'}$ are as defined above, is enantioselectively reduced with borane or another hydroboration agent in the presence of an optically active oxazaborolidine of the formula

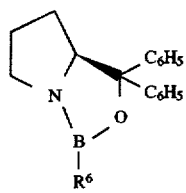

or its mirror image, where $R^6$ is hydrogen, $C_1$–$C_4$-alkyl or phenyl, to give the corresponding metallocenylalcohol of the general formula

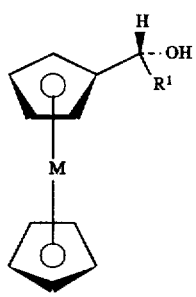

or

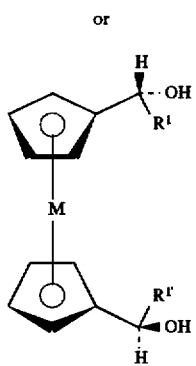

or its mirror image, where $R^1$ and $R^{1'}$ are as defined above, this is, after esterifying the hydroxy group, reacted with a secondary amine of the general formula $HNR^2R^3$ (V), where $R^2$ and $R^3$ are as defined above, to give the corresponding metallocenylamine of the general formula

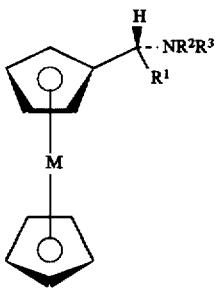

or

-continued

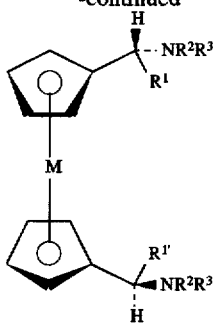

or its mirror image, where M and $R^1$ to $R^3$ are as defined above, and this is finally converted by lithiation and subsequent reaction with a halophosphine of the general formula $$X\,PR^4R^5 \qquad \text{VII}$$

where $R^4$ and $R^5$ are as defined above and X is chlorine, bromine or iodine, into the target compound.

2. The process according to claim 1, wherein the acylmetallocene (II) used is an acylferrocene.

3. The process according to claim 2, wherein the acylmetallocene (II) used is an acetylmetallocene.

4. The process according to claim 3, wherein the oxazaborolidine (III) in which $R^6$ is hydrogen is prepared in situ from the corresponding optically active α,α-diphenyl-2-pyrrolidinomethanol and borane.

5. The process according to claim 4, wherein borane is used in the form of its adduct with dimethyl sulfide.

6. The process according to claim 5, wherein the hydroxy group of the metallocenylalkanol (IVa/IVb) is acetylated before the reaction with the secondary amine (V).

7. The process according to claim 6, wherein the secondary amine (V) used is dimethylamine.

8. The process according to claim 7, wherein the halophosphine used is chlorodiphenylphosphine.

9. Process for preparing optically active metallocenyldialkanols of the general formula

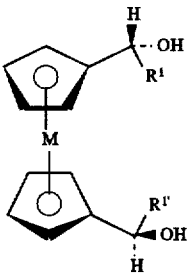

or its mirror image, where M, $R^1$ and $R^{1'}$ are as defined in claim 1, characterized in that a diacylmetallocene of the general formula

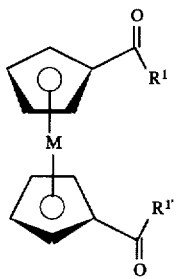

where M, $R^1$ and $R^{1'}$ are as defined above, is enantioselectively reduced with borane or another hydroboration agent in the presence of an optically active oxazaborolidine of the formula

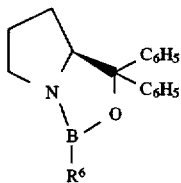

or its mirror image, where $R^6$ is hydrogen, $C_1$–$C_4$-alkyl or phenyl.

10. The process according to claim 9, wherein the diacylmetallocene (IIb) used is a diacylferrocene.

11. The process according to claim or 10, wherein the diacylmetallocene (IIb) used is a diacetylmetallocene.

12. The process according to claim 11, wherein the oxazaborolidine (III) in which $R^6$ is hydrogen is prepared in situ from the corresponding optically active α,α-diphenyl-2-pyrrolidinomethanol and borane.

13. The process according to claim 12, wherein borane is used in the form of an adduct with dimethyl sulfide.

14. The process according to claim 1, wherein the acylmetallocene (II) used is an acetylmetallocene.

15. The process according to claim 1, wherein the oxazaborolidine (III) in which $R^6$ is hydrogen is prepared in situ from the corresponding optically active α,α-diphenyl-2-pyrrolidinomethanol and borane.

16. The process according to claim 1, wherein borane is used in the form of its adduct with dimethyl sulfide.

17. The process according to claim 1, wherein the hydroxy group of the metallocenylalkanol (IVa/IVb) is acetylated before the reaction with the secondary amine (V).

18. The process according to claim 1, wherein the secondary amine (V) used is dimethylamine.

19. The process according to claim 1, wherein the halophosphine used is chlorodiphenylphosphine.

20. The process according to claim 9, wherein the diacylmetallocene (IIb) used is a diacetylmetallocene.

21. The process according to claim 9, wherein the oxazaborolidine (III) in which $R^6$ is hydrogen is prepared in situ from the corresponding optically active α,α-diphenyl-2-pyrrolidinomethanol and borane.

22. The process according to claim 9, wherein borane is used in the form of an adduct with dimethyl sulfide.

\* \* \* \* \*